(12) United States Patent
Mogensen et al.

(10) Patent No.: US 7,621,395 B2
(45) Date of Patent: Nov. 24, 2009

(54) PACKING FOR INFUSION SET AND METHOD OF APPLYING AN INFUSION SET

(75) Inventors: Lasse W. Mogensen, Søborg (DK); Jesper T. Olsen, København K (DK); Carl J. D. Åhman, Malmö (SE); May Britt Svendstrup, Viby Sjælland (DK); Steffen Gyrn, Ringsted (DK)

(73) Assignee: Unomedical A/S, Birkeroed (DK)

( * ) Notice: Subject to any disclaimer, the term of this patent is extended or adjusted under 35 U.S.C. 154(b) by 115 days.

(21) Appl. No.: 11/450,807

(22) Filed: Jun. 8, 2006

(65) Prior Publication Data

US 2007/0021729 A1    Jan. 25, 2007

Related U.S. Application Data

(60) Provisional application No. 60/694,547, filed on Jun. 28, 2005.

(30) Foreign Application Priority Data

Jun. 28, 2005   (DK) ............................... 2005 00958

(51) Int. Cl.
*B65D 83/10* (2006.01)
*A61B 17/06* (2006.01)
*A61M 37/00* (2006.01)
*A61M 5/178* (2006.01)

(52) U.S. Cl. ...................... 206/365; 206/367; 206/438; 206/571; 604/93.01; 604/167.02

(58) Field of Classification Search ......... 206/363–366, 206/368–370, 438–439, 570–572, 367; 604/93.01, 604/158–171, 500–506, 157; 220/359.1, 220/359.2
See application file for complete search history.

(56) References Cited

U.S. PATENT DOCUMENTS 643,544 A    2/1900   Simmons (Continued)

FOREIGN PATENT DOCUMENTS

DE        893 296        12/1953

(Continued)

*Primary Examiner*—Bryon P Gehman
(74) *Attorney, Agent, or Firm*—Brinks Hofer Gilson & Lione

(57) ABSTRACT

The present invention relates to a packing for an infusion set. The infusion set for intermittent or continuous administration of a therapeutic substance, such as insulin, includes an infusion part having a cannula penetrating the skin of a patient and a connector which connects the infusion part with a medical device such as an adaptor for a syringe or an insulin pump. The insertion of the infusion part will be performed with an insertion needle which is delivered together with the infusion part under sterile conditions. The packaging includes an impenetrable part protecting the surroundings from the insertion needle and a removal part which is to be removed by the user before applying the infusion part. The inner surface of the impenetrable part is provided with a retainer for releasable retaining at least a part of the infusion set.

23 Claims, 17 Drawing Sheets

U.S. PATENT DOCUMENTS

| | | |
|---|---|---|
| 1,838,825 A | 12/1931 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |
| 2,952,420 A | 9/1960 | Von Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,221,739 A * | 12/1965 | Rosenthal .................. 206/367 |
| 3,221,740 A * | 12/1965 | Rosenthal .................. 206/367 |
| 3,317,166 A | 5/1967 | Janssen |
| 3,485,352 A * | 12/1969 | Pilger ........................ 206/365 |
| 3,545,286 A | 12/1970 | Stenstrom |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,942,528 A | 3/1976 | Loeser |
| 3,986,508 A | 10/1976 | Barrington |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,267,836 A | 5/1981 | Whitney et al. |
| 4,306,705 A | 12/1981 | Svenson |
| 4,315,505 A | 2/1982 | Crandall et al. |
| 4,334,551 A | 6/1982 | Pfister |
| D267,199 S | 12/1982 | Koenig |
| 4,365,630 A | 12/1982 | McFlarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,473,369 A | 9/1984 | Lueders et al. |
| 4,500,312 A | 2/1985 | McFarlane |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,727,999 A | 3/1988 | Gach |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,890,608 A | 1/1990 | Steer |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,045 A | 2/1991 | Ranford |
| 5,011,475 A | 4/1991 | Olson |
| 5,020,665 A * | 6/1991 | Bruno ........................ 206/366 |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,134,593 A | 7/1992 | Logan et al. |
| 5,134,594 A | 7/1992 | Woo |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,172,808 A * | 12/1992 | Bruno ........................ 206/366 |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |

| | | | | | | |
|---|---|---|---|---|---|---|
| 5,429,607 A | 7/1995 | McPhee | | 6,074,371 A | 6/2000 | Fischell |
| 5,429,613 A | 7/1995 | D'Amico | | 6,086,008 A | 7/2000 | Gray et al. |
| 5,433,307 A | 7/1995 | Jeppe | | 6,086,575 A | 7/2000 | Mejslov |
| D362,718 S | 9/1995 | Deily et al. | | 6,090,068 A | 7/2000 | Chanut |
| 5,449,349 A | 9/1995 | Sallee et al. | | 6,093,172 A | 7/2000 | Funderburk et al. |
| 5,487,506 A | 1/1996 | Drummond et al. | | 6,093,179 A | 7/2000 | O'Hara et al. |
| 5,490,841 A | 2/1996 | Landis | | 6,099,503 A | 8/2000 | Stradella |
| 5,492,313 A | 2/1996 | Pan et al. | | 6,105,218 A | 8/2000 | Reekie |
| 5,505,709 A | 4/1996 | Funderburk et al. | | 6,120,482 A | 9/2000 | Szabo |
| 5,507,730 A | 4/1996 | Haber et al. | | 6,123,690 A | 9/2000 | Mejslov |
| 5,519,167 A | 5/1996 | Kunimoto et al. | | 6,132,755 A | 10/2000 | Eicher et al. |
| 5,520,654 A | 5/1996 | Wahlberg | | 6,183,464 B1 | 2/2001 | Sharp et al. |
| 5,522,803 A | 6/1996 | Teissen-Simony | | 6,193,694 B1 | 2/2001 | Bell et al. |
| 5,533,974 A | 7/1996 | Gaba | | 6,219,574 B1 | 4/2001 | Cormier et al. |
| 5,540,709 A | 7/1996 | Ramel | | 6,221,058 B1 | 4/2001 | Kao et al. |
| 5,545,143 A | 8/1996 | Fischell | | 6,248,093 B1 | 6/2001 | Moberg |
| 5,545,152 A | 8/1996 | Funderburk et al. | | 6,293,925 B1 | 9/2001 | Safabash et al. |
| 5,554,130 A | 9/1996 | McDonald et al. | | 6,302,866 B1 | 10/2001 | Marggi |
| 5,558,650 A | 9/1996 | McPhee | | 6,319,232 B1 | 11/2001 | Kashmer |
| 5,562,636 A | 10/1996 | Utterberg | | 6,322,535 B1 | 11/2001 | Hitchins et al. |
| 5,584,813 A | 12/1996 | Livingston et al. | | 6,322,808 B1 | 11/2001 | Trautman et al. |
| 5,591,188 A | 1/1997 | Waisman | | 6,334,856 B1 | 1/2002 | Allen et al. |
| 5,599,309 A | 2/1997 | Marshall et al. | | 6,355,021 B1 | 3/2002 | Nielsen et al. |
| 5,599,315 A | 2/1997 | McPhee | | 6,379,335 B1 | 4/2002 | Rigon et al. |
| 5,599,318 A | 2/1997 | Sweeney et al. | | D456,692 S | 5/2002 | Epstein |
| 5,628,765 A | 5/1997 | Morita | | 6,387,076 B1 | 5/2002 | Van Lunduyt |
| 5,643,214 A | 7/1997 | Marshall | | 6,387,078 B1 | 5/2002 | Gillespie, III |
| 5,643,216 A | 7/1997 | White | | 6,405,876 B1 | 6/2002 | Seshimoto et al. |
| 5,643,220 A | 7/1997 | Cosme | | 6,488,663 B1 | 12/2002 | Steg |
| 5,662,617 A | 9/1997 | Odell et al. | | 6,517,517 B1 | 2/2003 | Farrugia et al. |
| 5,665,071 A | 9/1997 | Wyrick | | 6,520,938 B1 | 2/2003 | Funderburk et al. |
| 5,665,075 A | 9/1997 | Gyure et al. | | D472,316 S | 3/2003 | Douglas et al. |
| 5,681,323 A | 10/1997 | Arick | | D472,630 S | 4/2003 | Douglas et al. |
| 5,695,476 A | 12/1997 | Harris | | 6,572,586 B1 | 6/2003 | Wojcik |
| 5,704,920 A | 1/1998 | Gyure | | 6,579,267 B2 | 6/2003 | Lynch et al. |
| 5,709,516 A | 1/1998 | Peterson et al. | | 6,582,397 B2 | 6/2003 | Alesi et al. |
| 5,714,225 A | 2/1998 | Hansen et al. | | 6,595,962 B1 | 7/2003 | Perthu |
| 5,741,288 A | 4/1998 | Rife | | 6,607,509 B2 | 8/2003 | Bobroff et al. |
| 5,752,923 A | 5/1998 | Terwilliger | | 6,607,511 B2 | 8/2003 | Bobroff et al. |
| 5,810,835 A | 9/1998 | Ryan et al. | | 6,629,949 B1 | 10/2003 | Douglas |
| 5,820,598 A | 10/1998 | Gazza et al. | | 6,645,182 B1 | 11/2003 | Szabo |
| D402,538 S | 12/1998 | Wagter et al. | | 6,659,982 B2 | 12/2003 | Douglas et al. |
| 5,843,001 A | 12/1998 | Goldenberg | | 6,685,674 B2 | 2/2004 | Douglas et al. |
| 5,851,197 A | 12/1998 | Marano et al. | | 6,702,779 B2 | 3/2004 | Connelly et al. |
| 5,858,001 A | 1/1999 | Tsals et al. | | 6,726,649 B2 | 4/2004 | Swenson et al. |
| 5,865,806 A | 2/1999 | Howell | | 6,736,797 B1 | 5/2004 | Larsen et al. |
| 5,873,540 A | 2/1999 | Hardin | | 6,749,589 B1 | 6/2004 | Douglas et al. |
| 5,899,886 A | 5/1999 | Cosme | | 6,790,199 B1 | 9/2004 | Gianakos |
| 5,913,846 A | 6/1999 | Szabo | | 6,805,686 B1 | 10/2004 | Fathallah et al. |
| 5,915,640 A | 6/1999 | Wagter et al. | | 6,811,545 B2 | 11/2004 | Vaillancourt |
| 5,916,199 A | 6/1999 | Miles | | 6,814,720 B2 | 11/2004 | Olsen et al. |
| 5,919,167 A | 7/1999 | Mulhauser et al. | | 6,824,530 B2 | 11/2004 | Wagner et al. |
| 5,925,032 A | 7/1999 | Clements | | 6,824,531 B1 | 11/2004 | Zecha, Jr. et al. |
| 5,947,935 A | 9/1999 | Rinehart et al. | | 6,830,562 B2 | 12/2004 | Mogensen et al. |
| 5,951,523 A | 9/1999 | Osterlind et al. | | 6,837,877 B2 | 1/2005 | Zurcher |
| 5,954,643 A | 9/1999 | VanAntwerp et al. | | 6,840,922 B2 | 1/2005 | Nielsen et al. |
| 5,957,892 A | 9/1999 | Thorne | | 6,880,701 B2 | 4/2005 | Bergeron et al. |
| 5,968,011 A | 10/1999 | Larsen et al. | | 6,916,017 B2 | 7/2005 | Noe |
| 5,975,120 A | 11/1999 | Novosel | | 6,923,791 B2 | 8/2005 | Douglas |
| 5,980,488 A | 11/1999 | Thorne | | 6,926,694 B2 | 8/2005 | Marano-Ford et al. |
| 5,980,506 A | 11/1999 | Mathiasen | | 6,939,331 B2 | 9/2005 | Ohshima |
| 5,984,224 A | 11/1999 | Yang | | 6,949,084 B2 | 9/2005 | Marggi et al. |
| 5,984,897 A | 11/1999 | Peterson et al. | | 6,959,812 B2 * | 11/2005 | Reif et al. .................. 206/438 |
| 5,992,787 A | 11/1999 | Burke | | 6,960,193 B2 | 11/2005 | Rosenberg |
| D417,733 S | 12/1999 | Howell et al. | | 6,991,619 B2 | 1/2006 | Marano-Ford et al. |
| 6,017,328 A | 1/2000 | Fischell et al. | | 6,991,620 B2 | 1/2006 | Marano-Ford et al. |
| D421,119 S | 2/2000 | Musgrave et al. | | 6,994,213 B2 * | 2/2006 | Giard et al. ................. 206/363 |
| 6,024,727 A | 2/2000 | Thorne et al. | | 7,022,108 B2 | 4/2006 | Marano-Ford et al. |
| 6,039,629 A | 3/2000 | Mitchell | | 7,055,713 B2 * | 6/2006 | Rea et al. .................... 220/276 |
| 6,042,570 A | 3/2000 | Bell et al. | | 7,303,543 B1 * | 12/2007 | Maule et al. ............. 604/93.01 |
| 6,045,533 A | 4/2000 | Kriesel et al. | | 7,309,326 B2 * | 12/2007 | Fangrow, Jr. ........... 604/167.02 |
| 6,050,976 A | 4/2000 | Thorne et al. | | 7,407,491 B2 * | 8/2008 | Fangrow, Jr. ........... 604/167.02 |
| 6,056,718 A | 5/2000 | Funderburk et al. | | 2001/0004970 A1 | 6/2001 | Hollister et al. |

| | | | | | | |
|---|---|---|---|---|---|---|
| 2001/0016714 A1 | 8/2001 | Bell et al. | | 2005/0101912 A1 | 5/2005 | Faust et al. |
| 2001/0021827 A1 | 9/2001 | Ferguson et al. | | 2005/0101932 A1 | 5/2005 | Cote et al. |
| 2001/0039401 A1 | 11/2001 | Ferguson et al. | | 2005/0101933 A1 | 5/2005 | Marrs et al. |
| 2001/0041875 A1 | 11/2001 | Higuchi et al. | | 2005/0107743 A1 | 5/2005 | Fangrow, Jr. |
| 2002/0022855 A1 | 2/2002 | Bobroff et al. | | 2005/0113761 A1 | 5/2005 | Faust et al. |
| 2002/0068904 A1 | 6/2002 | Pluth et al. | | 2005/0119637 A1 | 6/2005 | Lundgren et al. |
| 2002/0072720 A1 | 6/2002 | Hague et al. | | 2005/0124936 A1 | 6/2005 | Mogensen et al. |
| 2002/0077599 A1 | 6/2002 | Wojcik | | 2005/0131347 A1 | 6/2005 | Marano-Ford et al. |
| 2002/0082543 A1 | 6/2002 | Park et al. | | 2005/0159709 A1 | 7/2005 | Wilkinson |
| 2002/0107489 A1 | 8/2002 | Lee | | 2005/0215979 A1 | 9/2005 | Kornerup et al. |
| 2002/0111581 A1 | 8/2002 | Sasso | | 2005/0251098 A1 | 11/2005 | Wyss et al. |
| 2002/0145073 A1 | 10/2002 | Swanson | | 2005/0277892 A1 | 12/2005 | Chen |
| 2002/0156424 A1 | 10/2002 | Suzuki et al. | | 2005/0283114 A1 * | 12/2005 | Bresina et al. ........... 604/93.01 |
| 2002/0156427 A1 | 10/2002 | Suzuki et al. | | 2006/0030815 A1 | 2/2006 | Csincsura et al. |
| 2002/0161332 A1 | 10/2002 | Ramey | | 2006/0095003 A1 | 5/2006 | Marano-Ford et al. |
| 2002/0169419 A1 | 11/2002 | Steg | | | | |
| 2002/0173748 A1 | 11/2002 | McConnell et al. | | | FOREIGN PATENT DOCUMENTS | |
| 2002/0183688 A1 | 12/2002 | Lastovich et al. | | | | |
| 2002/0189688 A1 | 12/2002 | Roorda | | DE | 1 053 541 | 3/1959 |
| 2002/0193737 A1 | 12/2002 | Popovsky | | DE | 26 20 009 A1 | 12/1977 |
| 2002/0193744 A1 | 12/2002 | Alesi et al. | | DE | 28 03 509 A1 | 8/1979 |
| 2003/0060781 A1 | 3/2003 | Mogensen et al. | | DE | 196 31 921 A1 | 3/1997 |
| 2003/0069548 A1 | 4/2003 | Connelly et al. | | DE | 298 18 311 U1 | 3/1999 |
| 2003/0105430 A1 | 6/2003 | Lavi et al. | | DE | 19847143 A1 | 1/2000 |
| 2003/0109829 A1 | 6/2003 | Mogensen et al. | | DE | 299 21 406 U1 | 11/2001 |
| 2003/0125669 A1 | 7/2003 | Safabash et al. | | DE | 101 06 074 A1 | 6/2002 |
| 2003/0125678 A1 | 7/2003 | Swenson et al. | | DE | 203 20 207 U1 | 11/2004 |
| 2003/0130619 A1 | 7/2003 | Safabash et al. | | DK | DE 37 22 893 C1 | 6/1988 |
| 2003/0139704 A1 | 7/2003 | Lin | | DK | DE 38 23 447 C3 | 2/1996 |
| 2003/0158520 A1 | 8/2003 | Safabash et al. | | DK | DE 196 10 692 A1 | 9/1997 |
| 2003/0176843 A1 | 9/2003 | Wilkinson | | DK | DE 100 49 001 A1 | 4/2002 |
| 2003/0181863 A1 | 9/2003 | Davis et al. | | EP | 0 188 014 B1 | 10/1985 |
| 2003/0181868 A1 | 9/2003 | Swenson | | EP | 0 239 244 B1 | 2/1987 |
| 2003/0181873 A1 | 9/2003 | Swenson | | EP | 0 298 521 B1 | 9/1990 |
| 2003/0181874 A1 | 9/2003 | Bressler et al. | | EP | 0 184 231 B1 | 1/1992 |
| 2003/0187394 A1 | 10/2003 | Wilkinson et al. | | EP | 0 475 857 A1 | 3/1992 |
| 2003/0187395 A1 | 10/2003 | Wilkinson et al. | | EP | 0 544 837 B1 | 6/1993 |
| 2003/0199823 A1 | 10/2003 | Bobroff et al. | | EP | 0 633 039 A1 | 7/1994 |
| 2003/0216686 A1 | 11/2003 | Lynch et al. | | EP | 0 651 662 B1 | 5/1995 |
| 2003/0225373 A1 | 12/2003 | Bobroff et al. | | EP | 0 714 631 B1 | 6/1996 |
| 2003/0225374 A1 | 12/2003 | Mathiasen | | EP | 744 183 A2 | 11/1996 |
| 2003/0229308 A1 | 12/2003 | Tsals et al. | | EP | 0 747 006 A1 | 12/1996 |
| 2003/0229316 A1 | 12/2003 | Hwang et al. | | EP | 0 688 232 B1 | 12/1998 |
| 2004/0002682 A1 | 1/2004 | Kovelman et al. | | EP | 0 884 108 A1 | 12/1998 |
| 2004/0006316 A1 | 1/2004 | Patton | | EP | 0 916 361 A1 | 5/1999 |
| 2004/0026840 A1 | 2/2004 | Eckel et al. | | EP | 0 931 560 A1 | 7/1999 |
| 2004/0044306 A1 | 3/2004 | Lynch et al. | | EP | 0 956 879 A1 | 11/1999 |
| 2004/0049159 A1 | 3/2004 | Barrus et al. | | EP | 1 045 145 A1 | 10/2000 |
| 2004/0068231 A1 | 4/2004 | Blondeau | | EP | 1 060 757 A1 | 12/2000 |
| 2004/0087913 A1 | 5/2004 | Rogers et al. | | EP | 1 086 718 A1 | 3/2001 |
| 2004/0111068 A1 | 6/2004 | Swenson | | EP | 1 125 593 A1 | 8/2001 |
| 2004/0112781 A1 | 6/2004 | Hofverberg et al. | | EP | 1 167 765 A2 | 1/2002 |
| 2004/0116865 A1 | 6/2004 | Bengtsson | | EP | 0 775 501 B1 | 6/2002 |
| 2004/0138612 A1 | 7/2004 | Shermer et al. | | EP | 0 894 216 B1 | 7/2003 |
| 2004/0138620 A1 | 7/2004 | Douglas et al. | | EP | 1 360 970 A1 | 11/2003 |
| 2004/0143216 A1 | 7/2004 | Douglas et al. | | EP | 1 380 315 A1 | 1/2004 |
| 2004/0143218 A1 | 7/2004 | Das | | EP | 1 475 113 A1 | 11/2004 |
| 2004/0158202 A1 | 8/2004 | Jensen | | FR | 576849 | 8/1924 |
| 2004/0158207 A1 | 8/2004 | Hunn et al. | | FR | 2 611 013 A1 | 8/1988 |
| 2004/0162518 A1 | 8/2004 | Connelly et al. | | FR | 2725902 A1 | 10/1994 |
| 2004/0171989 A1 | 9/2004 | Horner et al. | | FR | 2733915 A1 | 11/1996 |
| 2004/0178098 A1 | 9/2004 | Swenson et al. | | FR | 2781617 A1 | 1/2000 |
| 2004/0186446 A1 | 9/2004 | Ohshima | | GB | 478803 | 1/1938 |
| 2004/0199123 A1 | 10/2004 | Nielsen | | GB | 591730 | 3/1946 |
| 2004/0204687 A1 | 10/2004 | Mogensen et al. | | GB | 906574 | 9/1962 |
| 2004/0204690 A1 | 10/2004 | Yashiro et al. | | GB | 1 268 575 | 3/1972 |
| 2004/0220528 A1 | 11/2004 | Garcia, Jr. | | GB | 1 403 034 | 8/1975 |
| 2004/0238392 A1 | 12/2004 | Peterson et al. | | GB | 2 224 808 A | 5/1990 |
| 2004/0243065 A1 | 12/2004 | McConnell et al. | | GB | 2 270 552 A | 3/1994 |
| 2004/0254433 A1 | 12/2004 | Bandis et al. | | JP | 5326062 A | 12/1993 |
| 2004/0260235 A1 | 12/2004 | Douglas | | JP | 7051251 | 11/1995 |
| 2004/0260250 A1 | 12/2004 | Harris et al. | | JP | 2000059877 A | 2/2000 |
| 2005/0035014 A1 | 2/2005 | Cane | | JP | 3140740 B2 | 3/2001 |

| | | | | | | |
|---|---|---|---|---|---|---|
| JP | 2002-028246 | 1/2002 | | WO | WO 01/30419 A2 | 5/2001 |
| NL | 1017427 C | 11/2002 | | WO | WO 01/68180 A1 | 9/2001 |
| WO | WO 87/06474 A1 | 11/1987 | | WO | WO 01/72353 A2 | 10/2001 |
| WO | WO 93/03787 A1 | 3/1993 | | WO | WO 01/81785 A1 | 11/2001 |
| WO | WO 93/05840 A2 | 4/1993 | | WO | WO 01/93926 A2 | 12/2001 |
| WO | WO 94/20160 A1 | 9/1994 | | WO | WO 02/46080 A1 | 6/2002 |
| WO | WO 95/28327 A1 | 10/1995 | | WO | WO 02/066854 A1 | 8/2002 |
| WO | WO 96/35472 A1 | 11/1996 | | WO | WO 02/068014 A2 | 9/2002 |
| WO | WO 98/09065 A1 | 3/1998 | | WO | WO 02/068014 A3 | 9/2002 |
| WO | WO 98/58693 A1 | 12/1998 | | WO | WO 02/094352 A2 | 11/2002 |
| WO | WO 99/07435 A1 | 2/1999 | | WO | WO 02/100457 A2 | 12/2002 |
| WO | WO 99/33504 A1 | 7/1999 | | WO | WO 03/015860 A1 | 2/2003 |
| WO | WO 99/36009 A1 | 7/1999 | | WO | WO 03/026728 A1 | 4/2003 |
| WO | WO 99/56802 A1 | 11/1999 | | WO | WO 2004/030726 A1 | 4/2004 |
| WO | WO 99/61815 A1 | 12/1999 | | WO | WO 2004/087240 A1 | 10/2004 |
| WO | WO 00/02614 A1 | 1/2000 | | WO | WO 2005/004973 A1 | 1/2005 |
| WO | WO 00/03757 A1 | 1/2000 | | WO | WO 2005/046780 A1 | 5/2005 |
| WO | WO 00/44324 A1 | 8/2000 | | WO | WO 2005/068006 A1 | 7/2005 |
| WO | WO 01/04507 A1 | 1/2001 | | | | |

* cited by examiner

SECTION B-B

US 7,621,395 B2

PACKING FOR INFUSION SET AND METHOD OF APPLYING AN INFUSION SET

This application claims the benefit of U.S. Provisional Application Ser. No. 60/694,547, filed Jun. 28, 2005 and is a continuation-in-part of Danish Application Serial No. PA 200500958, filed Jun. 28, 2005, these references are incorporated by reference herein in their entirety.

TECHNICAL FIELD

The present invention relates to a packaging for an infusion set. An infusion set for intermittent or continuous administration of a therapeutical substance, such as insulin, comprises an infusion part having a cannula penetrating the skin of a patient and a connector which connects the infusion part with a medical device such as an adaptor for a syringe or an insulin pump. The insertion of the infusion part will be performed with an insertion needle which is delivered together with the infusion part under sterile conditions.

BACKGROUND OF THE INVENTION

U.S. Pat. No. 5,968,011-A relates to a subcutaneous low-profile infusion set for, administrating a medication or a therapeutic fluid to a patient. It would be possible to apply this infusion set according to the present invention.

U.S. Pat. No. 6,355,021-B1 relates to a medical puncturing device. This device comprises a rigid needle mounted in a needle hub (2), and the needle hub comprises a handle part (3) and a shield part (4). This device could be used to insert an infusion set as described in U.S. Pat. No. 5,968,011-A.

US 2003/00130619 A1 relates to an insertion device and an insertion set. FIGS. 35 to 40 and the corresponding text ([0099]-[0107]) describe an insertion device which could be applied in connection with the present invention.

DESCRIPTION OF INVENTION

An object of the invention is to make insertion of an infusion device easier, more flexible and convenient for, the patient. According to the present invention it is possible to combine a standard infusion device with for example an inserter for automatic insertion or a handle for manual insertion as the inventive packaging assures the stability which is necessary in order to keep the infusion set and needle hub in position while a secondary device in the form of a handle or an inserter, chosen by the patient, is pushed against it and connected to it. When the packaging is used as a sort of handling device during the insertion procedure, the contamination of the infusion device is also kept at a minimum.

It is not essential whether the secondary device is connected releasable or unreleasable to the infusion device while connected to it as both possibilities have their advantages but the secondary device should form a stronger connection with the infusion set than the infusion set forms with the packaging according to the invention in order for the user to remove the infusion set from the packaging by simply pulling the secondary device away from the packaging.

One aspect of the invention concerns a packaging for an infusion set comprising an infusion part and a needle hub, where the needle hub is combined with an insertion needle. The packaging comprises an impenetrable part protecting the surroundings from the insertion needle and a removable part which is to be removed by the user before applying the infusion set wherein the inner surface of the impenetrable part is provided with means for releasable retaining at least a part of the infusion set.

Preferably the proximal side of the infusion set is provided with an adhesive, and the adhesive can be covered with a release layer.

In one embodiment of the invention the release layer covering the adhesive is partly fastened to the impenetrable part or fastened to a part being connected to the impenetrable part, an appropriate release layer for an adhesive sheet material is known from WO 2004/087240. This will cause the release layer to be removed when the infusion set and the needle hub is removed from the packaging. According to this embodiment the release layer can have the form of a band where one end of the band is fastened to the impenetrable part or fastened to a part being integrated with the impenetrable part.

In one embodiment of the invention the impenetrable part is made of a hard material. Preferably the impenetrable part is made of polypropylene (PP), polyethylene (PE HD) or PVC.

In one embodiment of the invention the needle hub is on its distal side provided with means for retaining a device. Preferably the needle hub is provided with means for retaining an inserter. More preferred the needle hub can take up and retain an inserter when the inserter is pushed towards the needle hub from the distal side. An inserter is not shown in the figures but a suitable inserter is described in US patent application no. 2003/0130619, FIGS. 35-38.

In a preferred embodiment the infusion set is releasably retained by the retaining means formed as an integrated part of the impenetrable part of the packaging. In this embodiment the infusion part can be provided with corresponding means which are releasable connected to the retaining means. According to this embodiment the retaining means can be formed as walls standing from the impenetrable part in an angle between −45° and 45° where 0° is orthogonal to the proximal surface of the impenetrable part, and the corresponding means can be formed as a cylinder or a truncated cone integrated with the infusion part.

In a most preferred embodiment the corresponding means comprise a cylinder or a truncated cone formed by a groove or recess in the infusion part making it possible for the proximal end of the corresponding means to be aligned to the proximal surface of the infusion part.

In another embodiment the retaining means are formed of a relatively soft material which material can be penetrated by the insertion needle and which soft material is connected unreleasable to the impenetrable part of the packaging.

In a preferred embodiment a support part parallel to the proximal surface of the infusion set is fastened to the impenetrable part or formed as an integrated part of the impenetrable part.

In another preferred embodiment the retaining means comprises an opening for the needle and a support part parallel to the proximal surface of the infusion set. In this embodiment the corresponding means can comprise a cylinder or a truncated cone protruding from the proximal surface of the infusion part.

The invention also concerns a method of applying an infusion set comprising an infusion part and a needle hub where the needle hub is combined with an insertion needle, which method comprises the following steps:

removing the removable part of the packaging, fastening a device to the needle hub, removing the infusion set from the impenetrable part of the packaging by pulling the device, and removing the release layer covering the adhesive if a release layer is present, placing the proximal end of the infusion set pointing against the skin of the user, penetrating the skin of the user by the insertion needle thereby positioning the infusion part, and securing the infusion set to the skin of the patient, removing the device and the needle hub leaving the infusion set in position.

In a preferred embodiment the method comprises the following steps:

removing the removable part of the packaging, fastening an inserter to the needle hub, removing the infusion set from the impenetrable part of the packaging by pulling the inserter, and removing the release layer covering the adhesive if a release layer is present, placing the proximal end of the infusion set pointing against the skin of the user, activating the inserter causing the insertion needle to penetrate the skin and position the infusion part, securing the infusion set to the skin of the patient, removing the inserter and the needle hub leaving the infusion set in position.

The invention also concerns a method of applying an infusion set comprising an infusion part and a needle hub where the needle hub is combined with an insertion needle, which method comprises the following steps:

removing the removable part of the packaging, X fastening a device to the needle hub, removing the infusion set from the impenetrable part of the packaging and removing the release layer covering the adhesive by pulling the device, placing the proximal end of the infusion set pointing against the skin of the user, penetrating the skin of the user by the insertion needle thereby positioning the infusion part, and securing the infusion set to the skin of the patient, removing the device and the needle hub leaving the infusion set in position.

It is possible to tighten or load the inserter/secondary device both before and after the infusion set has been removed from the impenetrable part of the packaging by pulling the device.

DESCRIPTION OF THE DRAWINGS

The invention is explained in greater detail below with reference to the accompanying drawings showing preferred embodiments of the inventions.

DEFINITION OF WORDS

"Distal side" refers to the side of the device which is turned away from the patient.

"Proximal side" refers to the side of the device which is turned towards the patient, and it will generally be used to describe the part of the device having a surface actually touching the patient.

"Integrated" refers e.g. in the phrase "fastened to a part being integrated with the impenetrable part" to that the part being integrated is connected unreleasable to the impenetrable part or e.g. formed of the same piece of material as the impenetrable part e.g. by molding "A hard material" as e.g. mentioned in claim 6, can resist a certain pressure without being deformed, at least the impenetrable part which is made of a hard material should be able to resist forces experienced within normal handling of the device.

"A relatively soft material" means that it is possible for the insertion needle (3) to penetrate the material in contrast to the hard material.

DESCRIPTION OF EMBODIMENTS

Figure 1A:
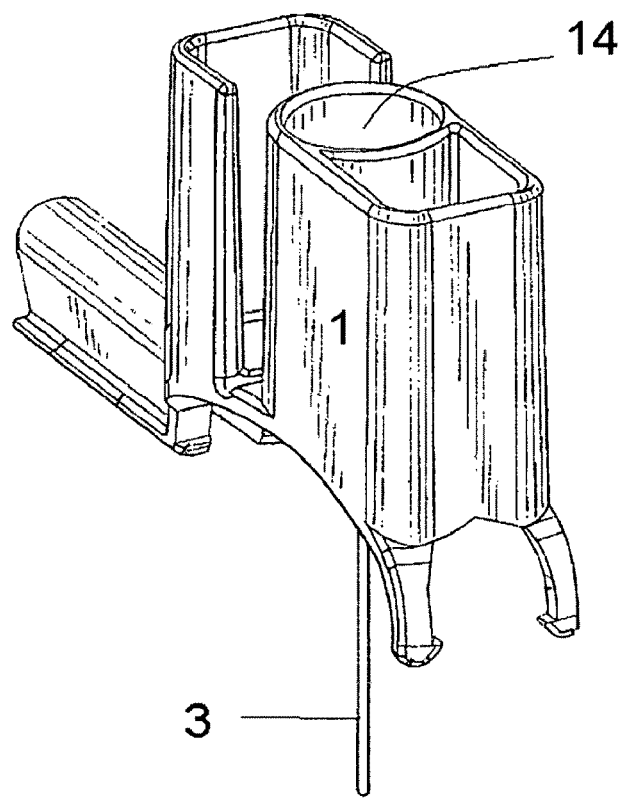
FIG. 1a shows a needle hub.

FIG. 1a shows an embodiment of a needle hub 1 with a rigid insertion needle 3 and means 14 for retaining a device which could be either a handle or an inserter. The means 14 in this embodiment comprise a cylindrical opening which opening can receive a corresponding form mounted on a handle or an inserter when the handle/inserter is pushed toward the needle hub 1. This embodiment of a needle hub is known from U.S. Pat. No. 6,355,021-B1.

Figure 1B:
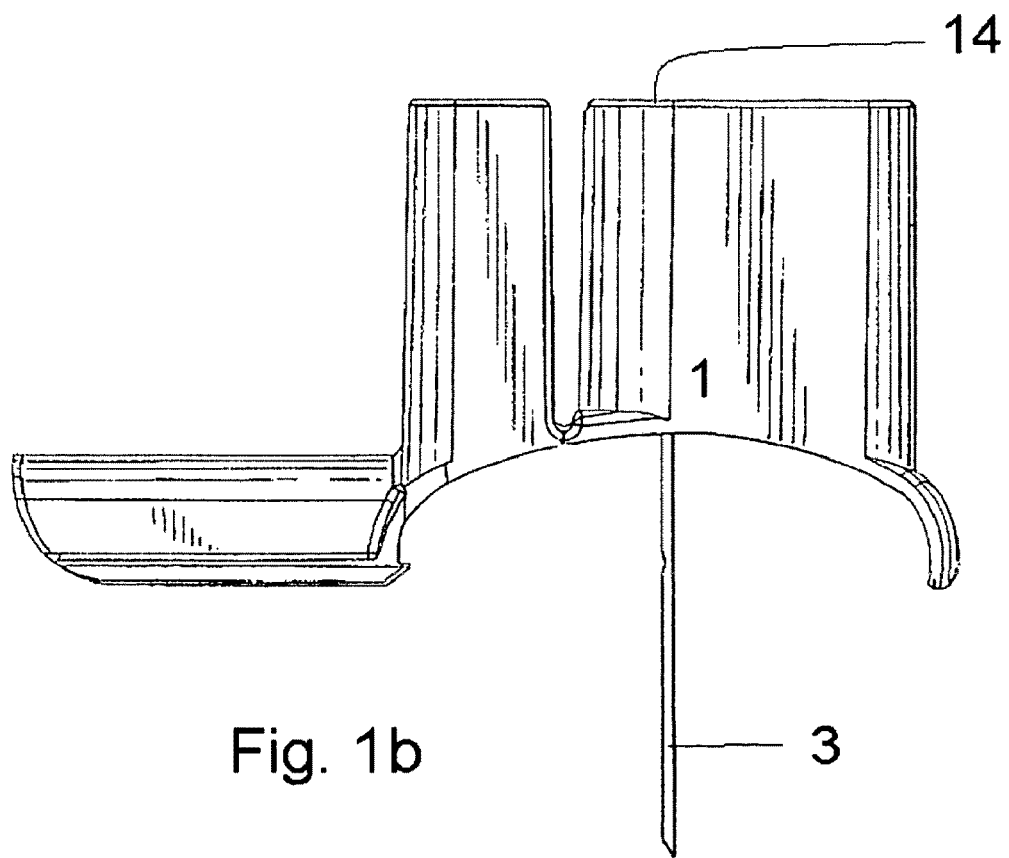
FIG. 1b shows the same needle hub from a different angle.

FIG. 1b shows the same needle hub as FIG. 1a seen from the side.

Figure 2:
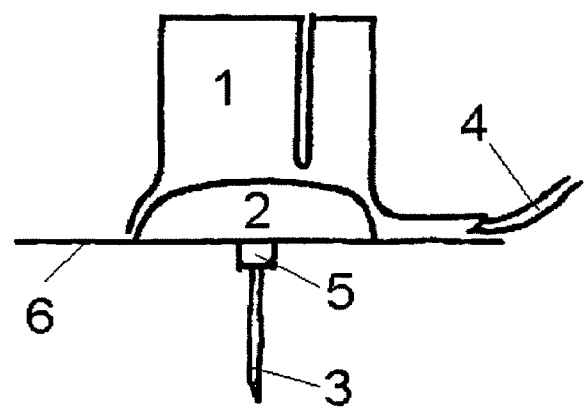
FIG. 2 shows a needle hub integrated with an infusion part.

FIG. 2 shows an embodiment of the same needle hub 1 as in FIGS. 1a and 1b combined with an infusion part 2. The infusion part can be in one piece comprising a soft cannula extending from the proximal side of the infusion part and a connection in the form of a tube 4 extending from the distal side of the infusion set. In the embodiment of FIG. 2 the connection is extending parallel to the patient's skin. The infusion part can also be a combination of two pieces, a part holding the cannula and a connector part, where a cannula is extending from the proximal side of the infusion part while the connection is extending from a distal side of the connector part. The infusion part 2 is formed with a center piece 5 on the proximal side. The center piece 5 can be extending relatively to the proximal surface of the infusion part 2 or the proximal side of the adhesive 6, as it is shown in FIG. 2, but it can also be retracted relatively to these surfaces. If the center piece 5 is retracted it can be formed by a circular groove or recess in the infusion part 2 surrounding the center piece 5.

An adhesive layer 6 preferably covered with a release layer 6a is unreleasably fastened to the proximal side of the infusion part 2. In the embodiment of FIG. 2 the cannula is adjoined to the insertion needle although the cannula is not actually shown in the figure.

Figure 3:
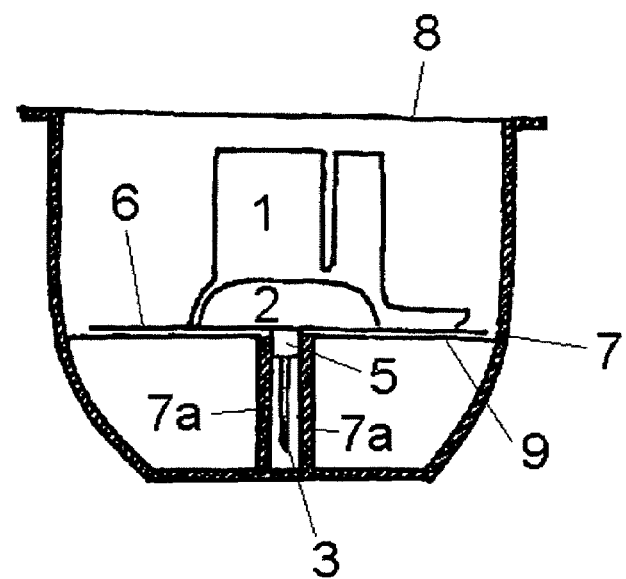
FIG. 3 shows an embodiment of the invention where a needle hub integrated with an infusion part is placed in a protecting packing.

FIG. 3 shows a combination comprising a needle hub 1 and an infusion part 2 in an embodiment of the inventive packaging 7, 8. The packaging comprises an impenetrable part 7 preferably formed of a relatively hard plastic such as polypropylene (PP), polyethylene (PE HD) or polyvinyl chloride (PVC). At least the impenetrable part 7 should be able to resist forces experienced within normal handling of the device without being deformed and/or penetrated by the insertion needle 3. The impenetrable part 7 covers the proximal side of the combination 1, 2 and due to the chosen material and also due to the positioning of the needle 3, as the needle 3 of the needle hub 1 is placed in a certain distance from the surface of the packaging, the impenetrable part 7 protects the surroundings from the needle. At least a part of the distal side of the combination 1, 2 is covered by a removable part 8 which is at least partly removed by the user before the device is applied.

When placed in the packaging the combination 1, 2 is in contact with a support part 9 which part is fastened to or being a part of the inner surface of the packaging. The support part 9 could be circular or in the form of one or more beams, and/or it could be fastened to either a central part reaching towards the periphery without actually touching the periphery or it could be fastened to the periphery reaching for the center. The support part 9 can also function as a release layer for the adhesive 6 meaning that the support part 9 totally or partly protects the adhesive surface during storage.

If the support part 9 functions as a release layer it is important to consider the force needed to overcome the release of the infusion part 2 from the support part 9 as the infusion part 2 in some degree is fastened to the support part 9 by adhesion. In order to regulate the attraction between the infusion part 2 and the support surface 9 and thereby also regulate the force needed to overcome the release of the infusion part 2, a suitable fraction of the adhesive 6 surface can be covered by a release layer which has no attraction to the support surface 9.

The support part 9 assures that the combination 1, 2 is positioned in a stable manner.

In a preferred embodiment the support part 9 has the form of a number of ribs fastened to or integrated with the walls of the impenetrable part 7, preferable the ribs are equally distributed along the inner surface of the impenetrable part 7 in order to offer maximum support for the infusion set. Also in a preferred embodiment the periphery of a spiral release layer 6a protecting the adhesive surface 6 is fastened to the impenetrable part 7 or to a part integrated with the impenetrable part 7. The spiral release layer 6a could be fastened to the impenetrable part 7 by gluing, welding or mechanically.

In this embodiment of the packaging the needle/cannula of the combination 1, 2 is placed in a circular center part 7a with walls standing upright from the inner surface of the impenetrable part 7. The center piece 5 is squeezed down into the corresponding circular center part 7a and the friction between the piece 5 and the walls in the center part 7a keeps the combination 1, 2 in place.

In another not shown embodiment means 7a comprises flat springs fastened to the periphery of the impenetrable part 7 and pushing down on parts of the infusion part 2 and/or parts of the needle hub 1. The flat springs can during production be pushed down over parts of the infusion device 2 and fastened to the periphery which will keep the combination 1, 2 in place.

In FIG. 3 the removable part 8 is made of a paper material e.g. Integra peel medical grade paper or heat seal coated Tyvek®, and the paper material is fastened to the upper edge of the impenetrable part 7. Before applying the device the user pulls of the removable part 8 making the combination accessible.

The connection in form of a tube 4 can be twined around the combination 1, 2 (not shown in the figures) which makes it possible to pull out the tube 4 without the tube getting tangled.

Figure 4:
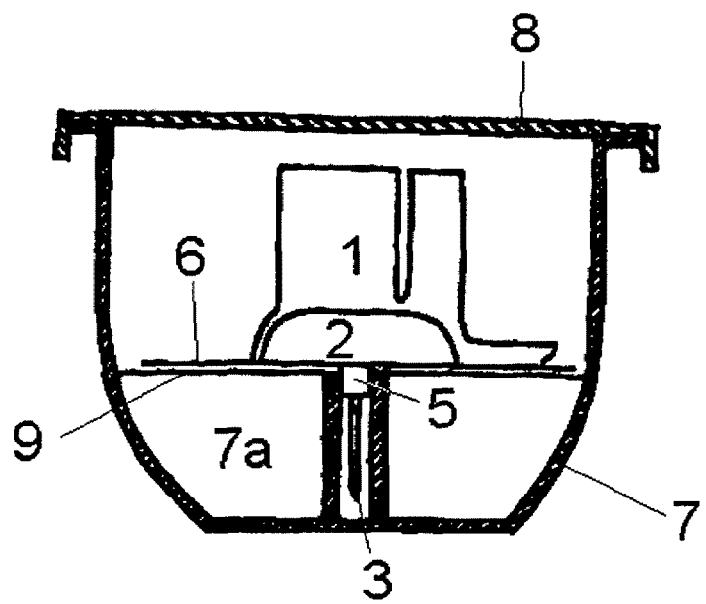
FIG. 4 shows a second embodiment of the invention where a needle hub integrated with an infusion part is placed in a protecting packing.

FIG. 4 shows another embodiment of the packaging where the removable part 8 is in the form of a relatively hard lid. Before applying the device the user will have to pull of the removable part 8 making the combination accessible.

Figure 5:
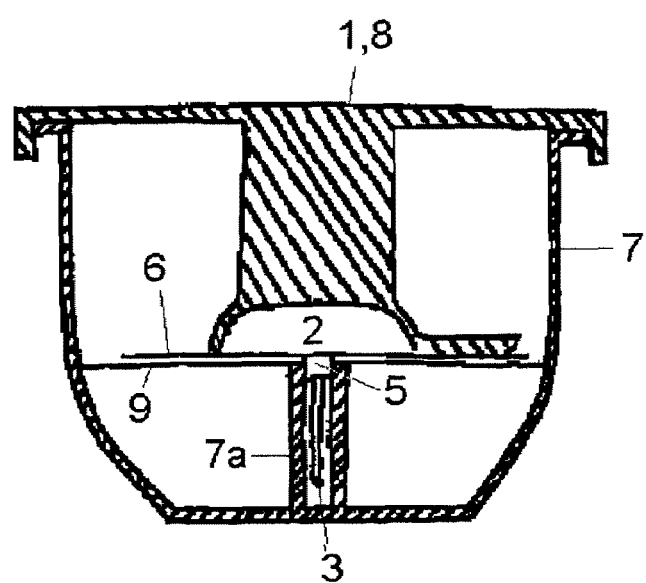
FIG. 5 shows a third embodiment of the invention where a needle hub integrated with an infusion part is placed in a protecting packing.

FIG. 5 shows an embodiment comprising a handle for manual insertion. The handle is formed by integrating the needle hub 1 with the removable part 8, either by creating the two parts as one or by connecting the two parts in a stable manner.

Figure 6:
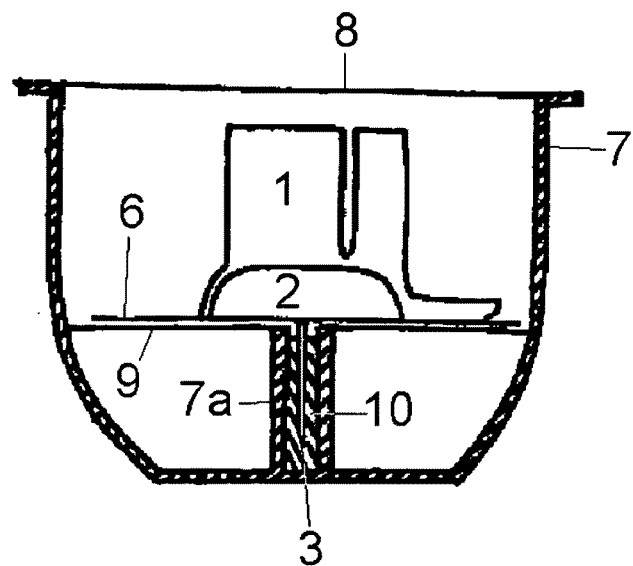
FIG. 6 shows a fourth embodiment of the invention where a needle hub integrated with an infusion part is placed in a protecting packing.

FIG. 6 shows an embodiment of the invention where the center piece 5 is replaced with a material 10 placed inside the circular center part 7a. In another not shown embodiment the lower part of the impenetrable part 7 is filled with this material 10, which e.g. can be silicone, to a height exceeding the length of the needle, in this embodiment the filling material 10 constitutes the support part 9. According to this solution the combination 1, 2 is kept in place by the friction between the needle and the filling material 10.

Figure 7:
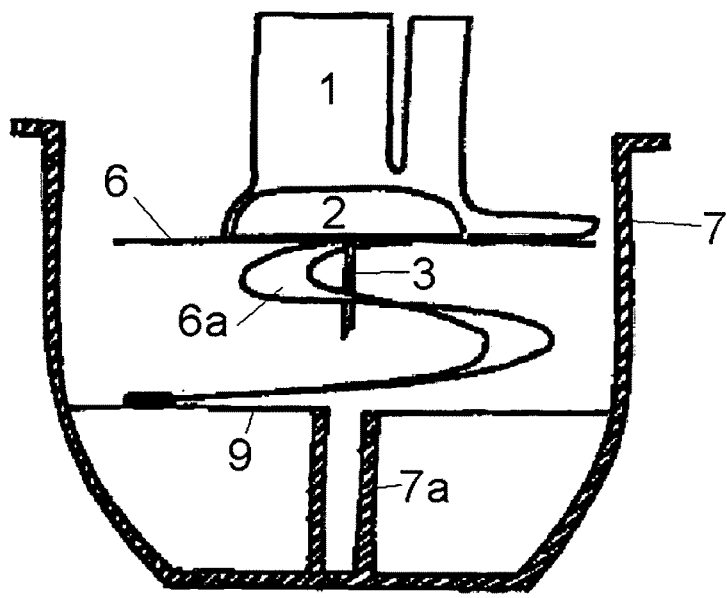
FIG. 7 shows an embodiment of the invention where a needle hub integrated with an infusion part is placed in a protecting packing provided with a feature for removal of the release paper.

FIG. 7 shows an embodiment of the invention where a release layer 6a covering the adhesive 6 is removed during release of the combination 1, 2 from the packaging. The release layer 6a is formed as a spiral band where one end—in this embodiment the end closest to the periphery—is connected to the support part 9, and the rest of the release layer 6a is releasably fastened to the adhesive surface 6.

The FIGS. 8a to 8f illustrate an embodiment of the invention and how this embodiment functions during use.

Figure 8A:
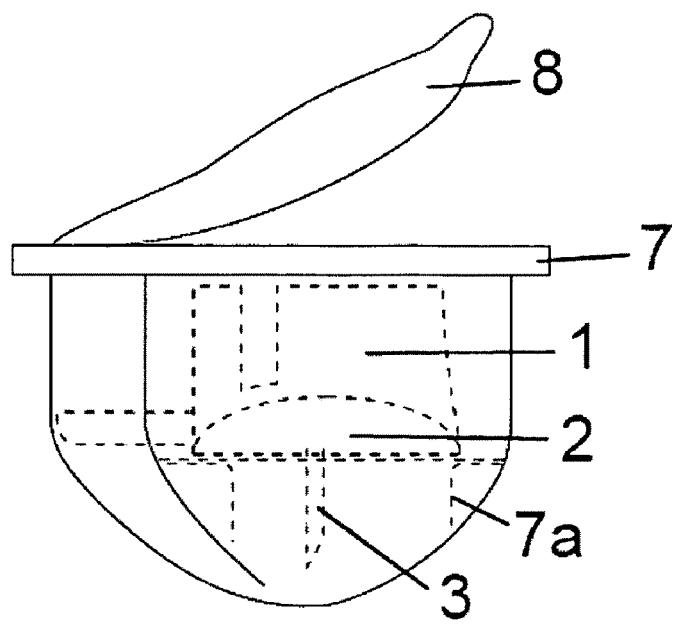
FIGS. 8a-8f illustrates a method of preparing the packaging and the needle hub and infusion part.

In FIG. 8a the combination of needle hub 1 and infusion part 2 is placed inside a packaging according to the invention under sterile conditions, and the impenetrable part 7 protects the surroundings from contact with the insertion needle 3. The removable part 8 is loosened from the distal edge formed by the impenetrable part 7 but is not totally removed.

Figure 8B:
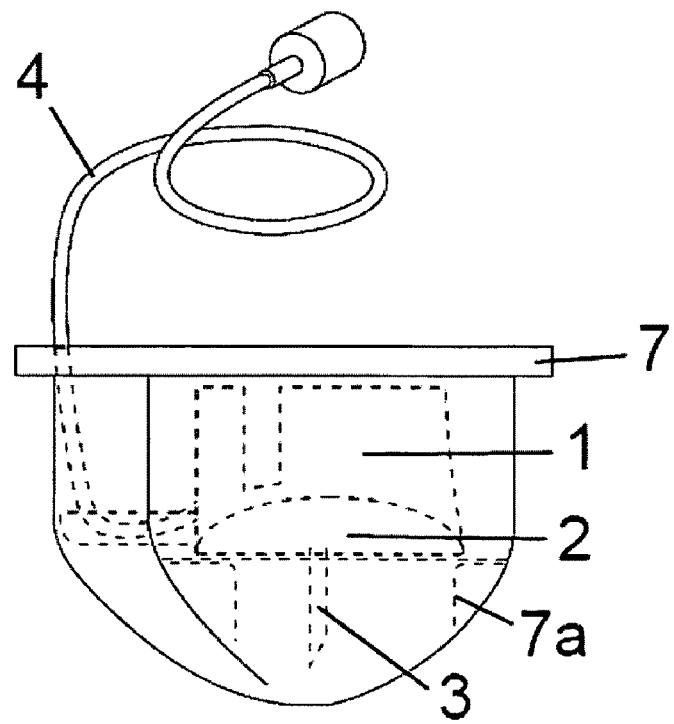

In FIG. 8b the removable part 8 has been totally removed and the tube 4 which is connected to the infusion part 2 has been pulled out of the packaging.

Figure 8C:
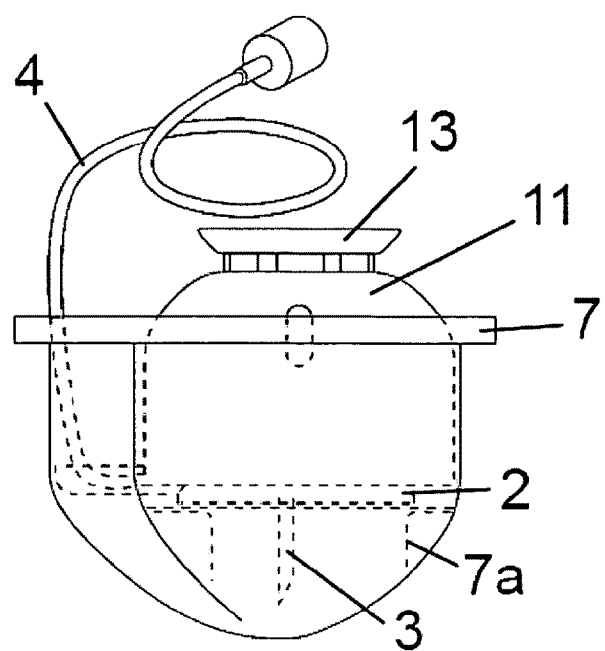

In FIG. 8c an inserter 11 with a handle 13 has been fastened to the needle hub 1 by pushing the inserter 11 towards the needle hub 1 through the opening that was revealed when the removable part 8 was removed. The inserter 11 comprises internal tracks corresponding to the means 14 of the needle hub 1, and when the inserter 11 is pushed toward the needle hub 1 in the right angle, the needle hub 1 will be pressed into the tracks of the inserter 11 causing the needle hub 1 and the inserter 11 to be fastened to each other.

Figure 8D:
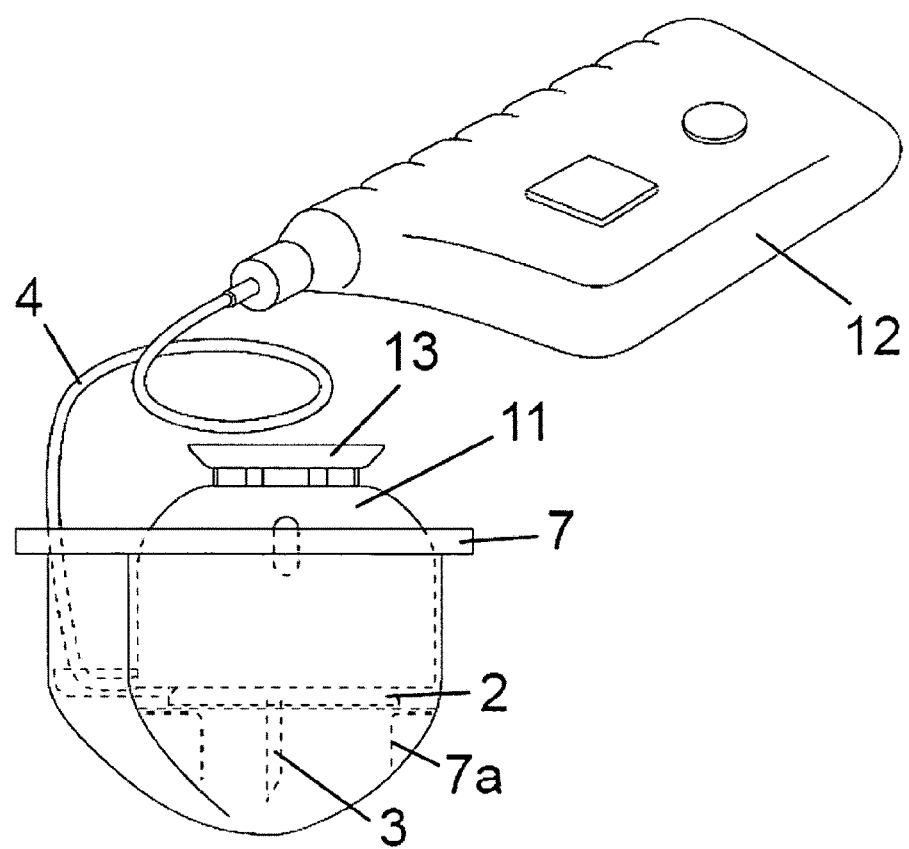

In FIG. 8*d* the tube 4 of the infusion device has been connected to a medical device 12 which in this embodiment has the form of an insulin pump.

Figure 8E:
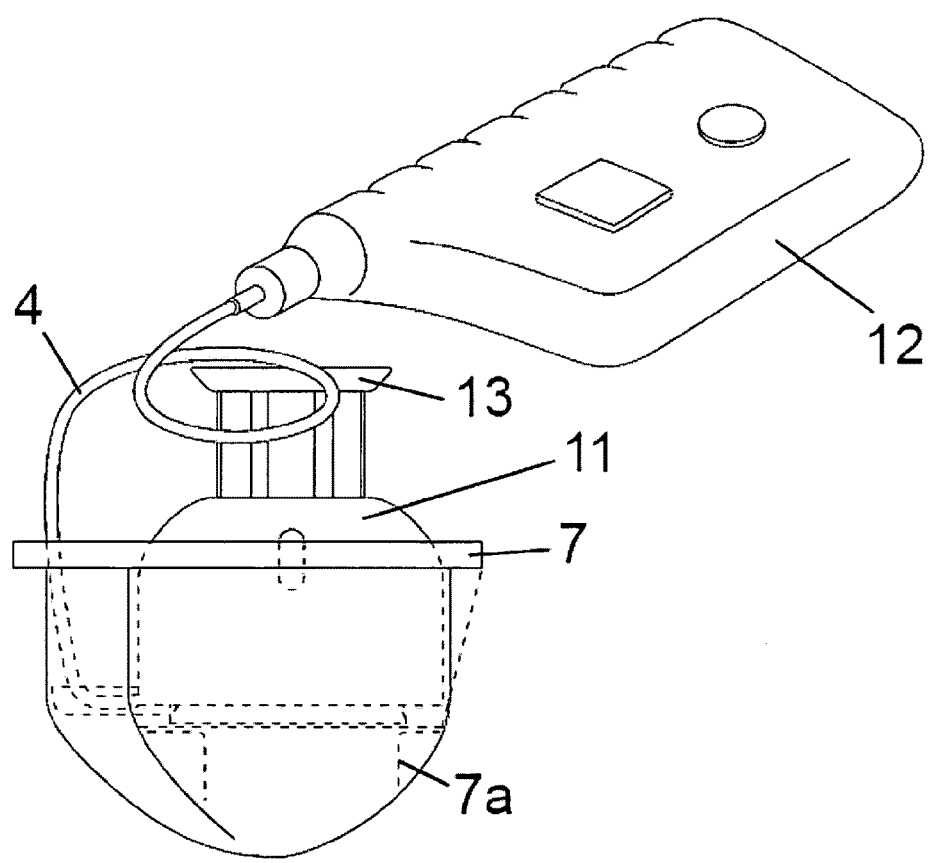

In FIG. 8*e* the inserter 11 has been prepared for insertion of the infusion set by pulling up the handle 13. The act of pulling up the handle could also be referred to as "tightening" or "loading" the inserter as an internal spring in the inserter is biased by this action. When preparing the inserter 11 the needle hub 1 and the infusion part 2 is released from the packaging and placed inside the inserter 11.

Figure 8F:
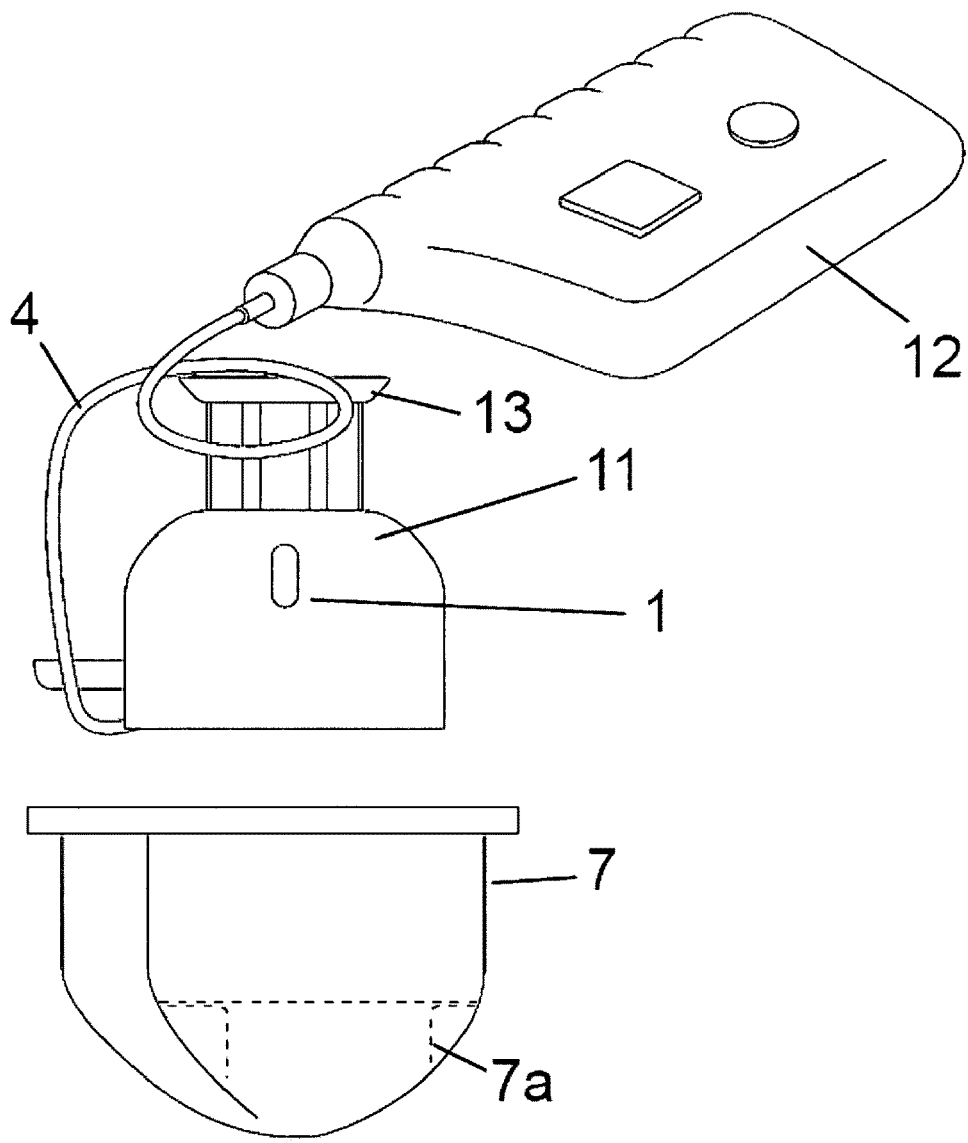

In FIG. 8*f* the infusion set connected to the inserter 11 is lifted out of the packaging and it is now ready for inserting the infusion set. When inserting the infusion set the user places the proximal end of the inserter 11 against the skin and thereafter the user activates the inserter 11 and causes the insertion needle 3 to penetrate the skin of the user. After insertion the inserter 11 is pulled away, and if the needle hub 1 to which the insertion needle 3 is fastened, is adequately secured to the inserter, the insertion needle 3 will be removed together with the inserter leaving only the infusion part 2 on the users skin.

Figure 9:
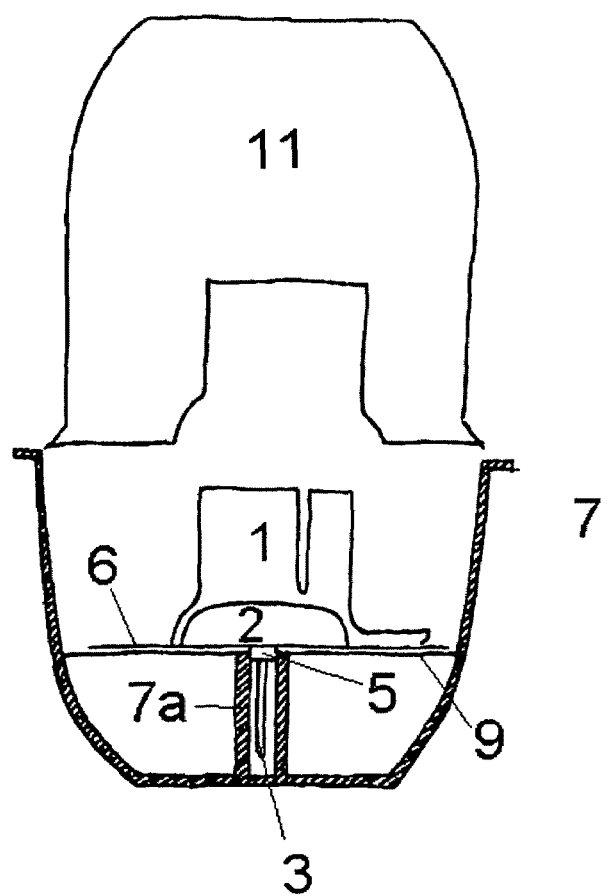
FIG. 9 shows an embodiment of the packaging together with an inserter just before attachment of the inserter.

FIG. 9 shows an embodiment of the packaging 7, 8 together with an inserter 11 just before the inserter 11 is fastened to the needle hub 1. In this embodiment the retaining means 7*a* squeezes very firmly around corresponding means—the central piece—5. In order to loosen the strong hold of the central piece 5 the internal form of the packaging is constructed in such a way that the pressing the inserter 11 down toward the needle hub 1 forces the sides of the impenetrable part 7 of packaging outwards.

Figure 10:
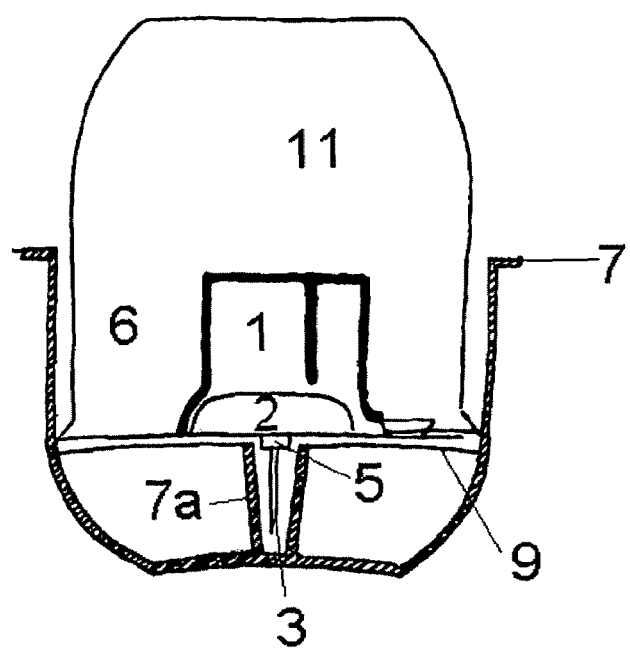
FIG. 10 shows an embodiment of the packaging together with an inserter just after the inserter has been fastened to the needle hub.

FIG. 10 shows the appearance of the impenetrable part 7 of the packaging after the inserter 11 has been pushed down over the needle hub 1. The diameter of the upright walls constituting the retaining means 7*a* has been extended and a result of this is that the force needed to pull the center piece 5 out of the retaining means 7*a* has been reduced.

Figure 11:
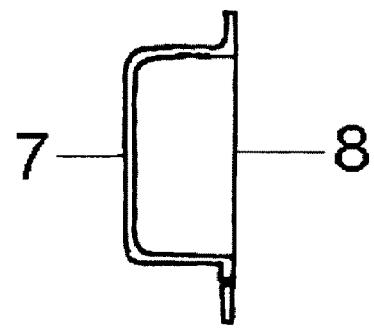
FIG. 11 shows an embodiment of the packaging provided with a preferred opening mechanism.
Figure 11:
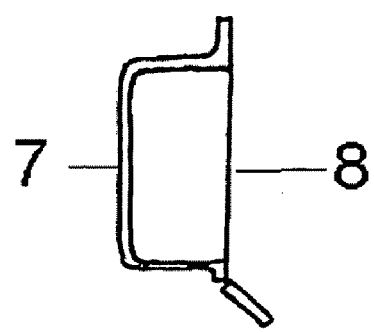
Figure 11:
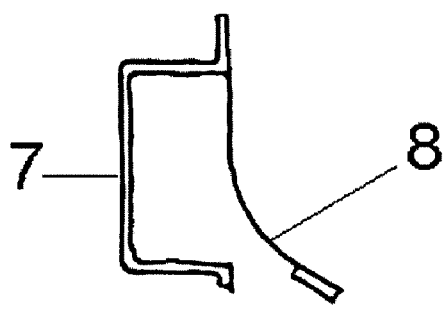

FIG. 11 shows an embodiment of the packaging with means for easy-opening. The impenetrable part 7 is provided with a top flange and the removable part 8 which is preferably made in paper, has been welded to the whole surface of the flange. A line of fracture 15 isolates a corner or a piece of the top flange of the impenetrable part 7 and when the user opens the packaging the corner/piece is broken of the top flange and the removable part which is not provided with a fractured line will be easily removed by pulling the in the broken off piece which is still welded to the piece of the removable part 8 covering the piece.

Figure 12:
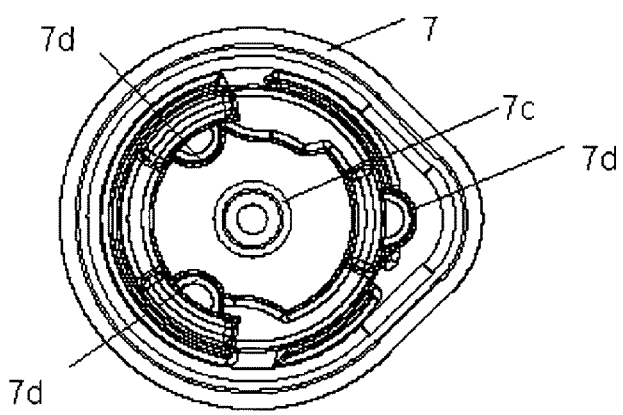
FIG. 12 shows an embodiment of the protecting packaging without needle hub seen from above where the packaging is provided with legs and a substantially centered protrusion for receiving a circular center part.
Figure 13:
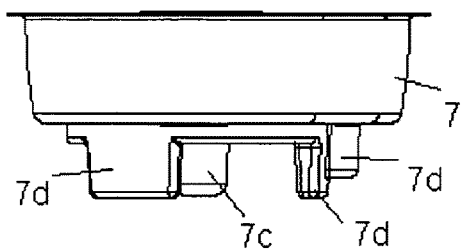
FIG. 13 shows a first sides view the embodiment of the packaging shown in FIG. 12.
Figure 14:
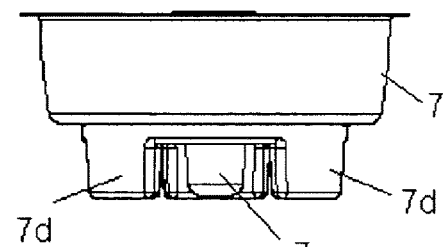
FIG. 14 shows a second side view of the embodiment of the packaging shown in FIG. 12.

FIGS. 12-14 shows a further embodiments of the packaging from the outside at three different angles. The impenetrable part 7 has an upper end which is provided with the removable part 8 and a lower end positioned opposite the upper end. FIG. 12 shows the packaging from above, meaning from the upper end of the impenetrable part 7 of the packaging, where FIGS. 13 and 14 shows two different side views of the packaging. This embodiment of the packaging according to FIGS. 12-14 shows the impenetrable part 7 being shaped with three legs 7*d* protruding from the lower surface of the impenetrable part (7) and a substantially centered shaped protrusion 7*c* inside which a separate center part 7*b* is positioned.

Figure 15:
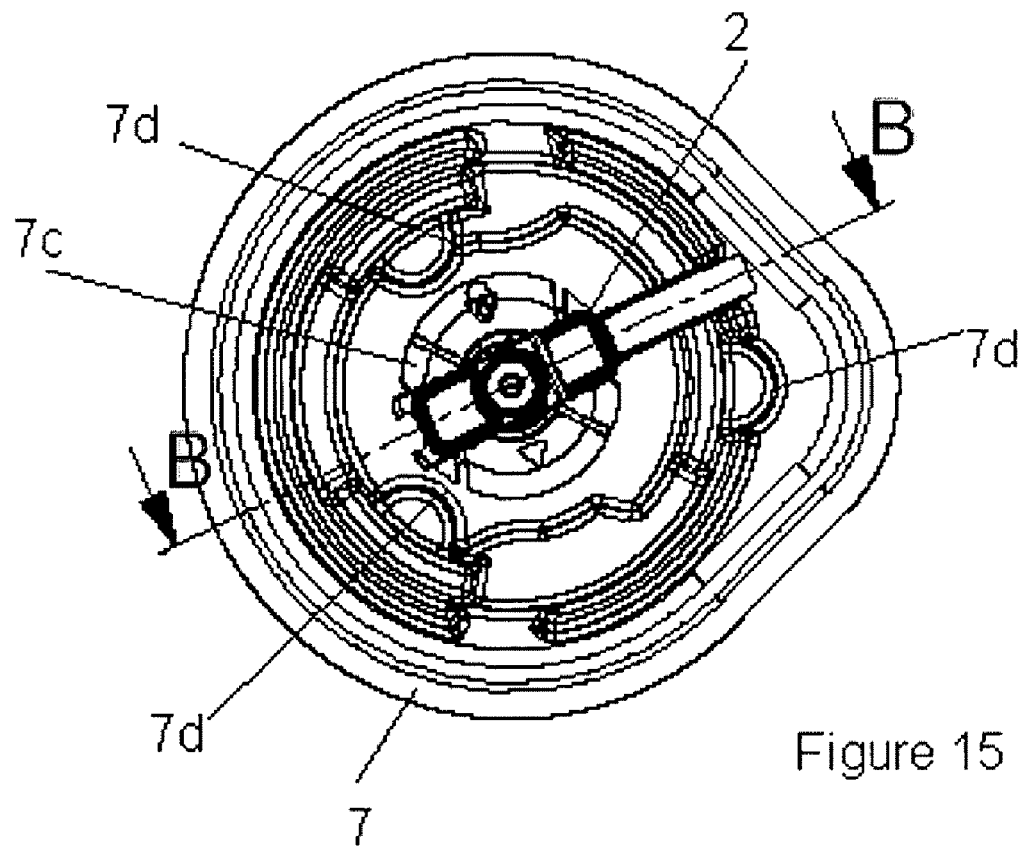
FIG. 15 shows an embodiment of the packaging together with an infusion device.

FIG. 15 shows an embodiment of the packaging where the needle/cannula of the combination 1, 2 is placed in the center part 7*b*. In this embodiment the center part 7*b* is circular and formed as a separate part. The center part 7*b* is placed upright from the inner surface of the impenetrable part 7 in a correspondingly shaped protrusion 7*c* in the impenetrable part 7 of the packaging. The separate center part 7*b* is lengthwise provided with a through-going slit 14, which makes the center part 7*b* elastic, i.e. it is possible to vary the dimension of the center part 7*b*. The center part 7*b* is placed in the correspondingly shaped protrusion 7*c* engaging with the center piece 5 of the impenetrable part 7. As the center piece 5 engages with the corresponding circular center part 7*b*, the center part 7*b* is expanded and the center part 7*b* is fixed in the protrusion 7*c*. The friction between the center piece 5 and the separate circular center piece 7*b* placed in the correspondingly shaped protrusion 7*c* in the impenetrable part 7 keeps the combination 1, 2 in place. Further, the friction occurring between the center part 7*b* and the protrusion 7*c* keeps the center part 7*b* within the protrusion 7*b* of the packaging, this friction being larger than the friction between the center piece 7*b* and the combination 1, 2.

Figure 16:
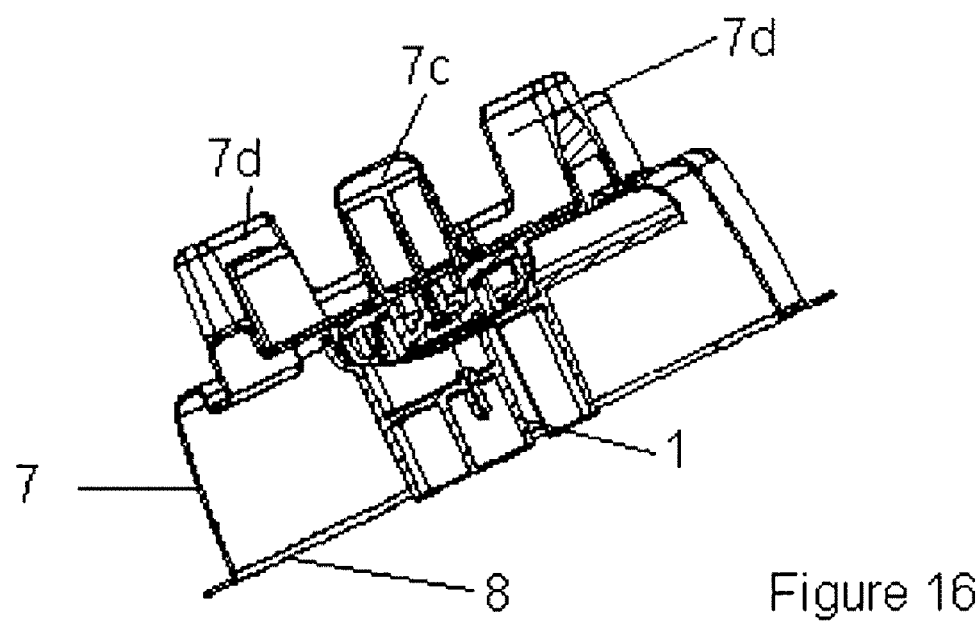
FIG. 16 shows a cross sectional view B-B of the embodiment shown in FIG. 15.

In preparing the infusion set for insertion the removable part 8 is removed from the impenetrable part 7 and the combined needle hub 1 and infusion part 2 is released from the packaging either manually or by an inserter 11 (FIG. 16). In order to loosen the strong hold of the center piece 5, the form of the separate center part 7*b* is constructed in such a way that the pressing of the inserter 11 down toward the needle hub 1 forces the center part 7*b* to expand outwards towards the protrusion 7*c* in the packaging, which is possible due to the slit which makes to center part 7*b* elastic.

Figure 17:
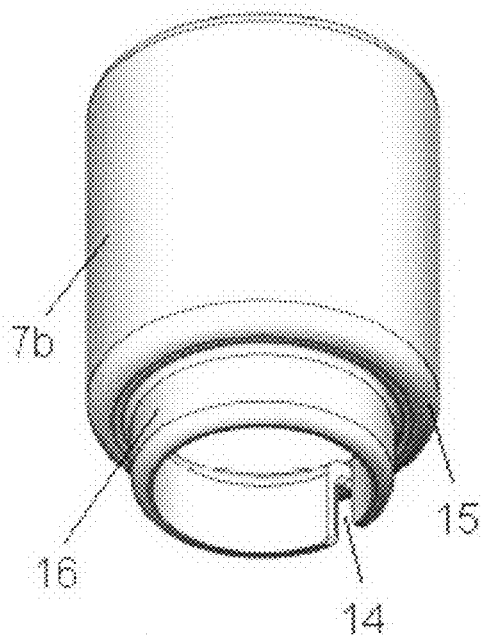
FIG. 17 shows an embodiment of the protecting packaging where the retaining means comprises a separate circular center part.
Figure 18:
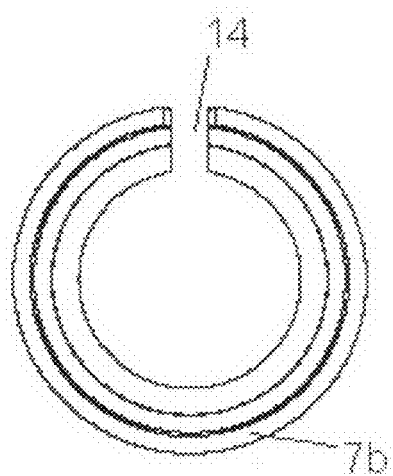
FIG. 18 shows a sectional view of the retaining means of FIG. 17.
Figure 19:
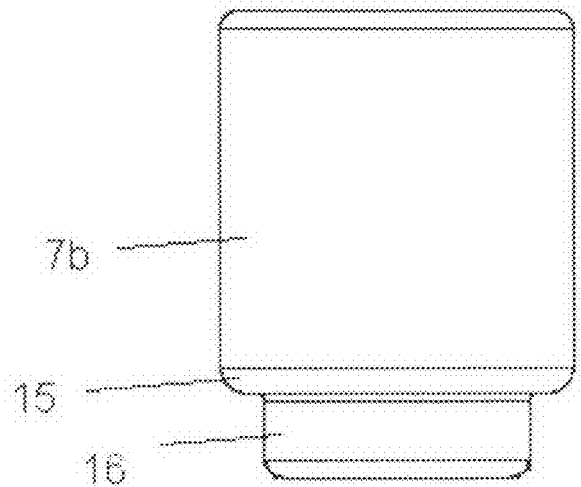
FIG. 19 shows a side view of the retaining means of FIG. 17.

FIGS. 17-19 shows a circular embodiment of the center part 7*b* with a lengthwise through-going slit 14. The circular center part 7*b* is in this embodiment provided with a circular part 16 having a smaller diameter than the diameter of the circular center part 7*b* via a shoulder part 15 which secures and keeps the center piece 5 in place.

Figure 20:
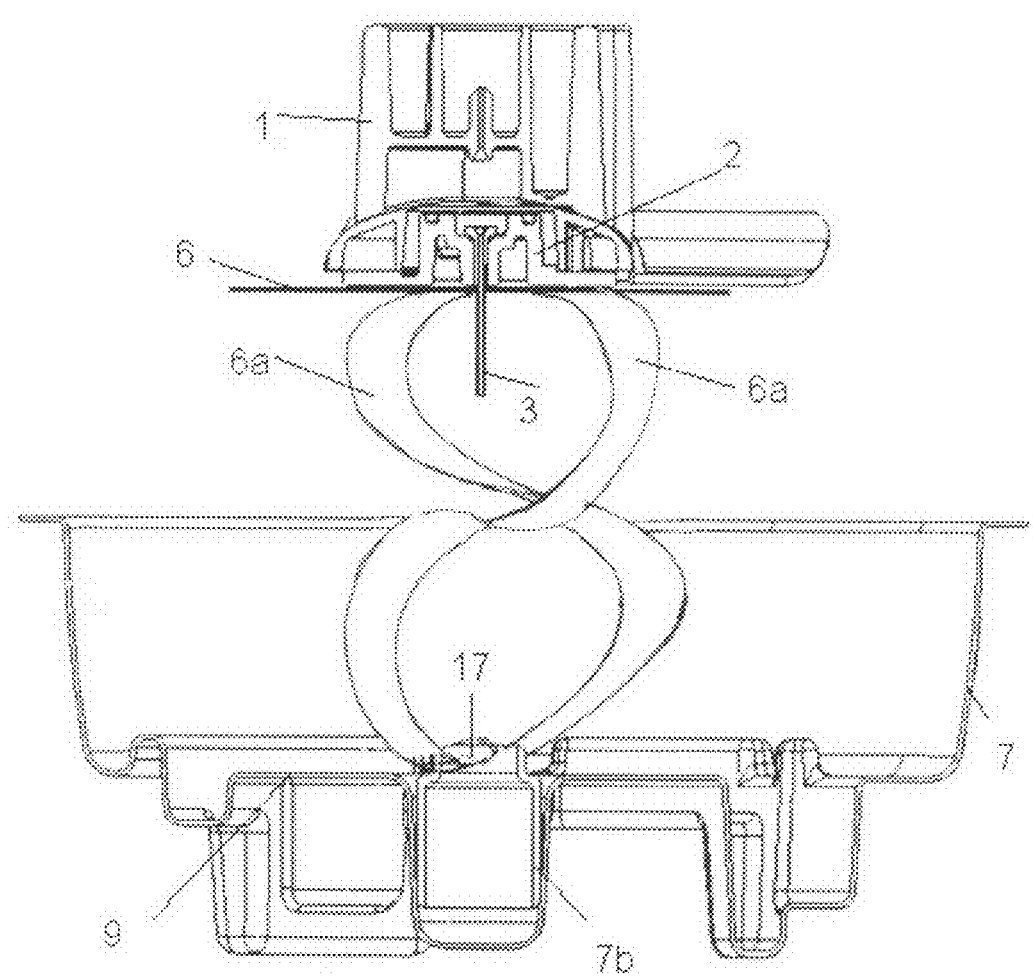
FIG. 20 shows an embodiment of where a known needle hub integrated with an infusion part is removed from a protecting packaging with a feature for removal of a double spiral release paper.

FIG. 20 shows an embodiment of the invention where a release layer 6*a* covering the adhesive 6 is removed during release of the combination 1, 2 from the packaging. The release layer 6*a* is in this embodiment divided into two sections where each section forms a strip such as a spiral band, thereby forming a double spiral release layer 6*a*. The peripheral end 17 of each strip of the release layer 6*a* closest to the periphery, only one is shown in the figure, are connected to the impenetrable part 7 or to a part integrated with the impenetrable part 7, and the rest of the release layer 6*a* is releasable fastened to the adhesive surface 6. As the above mentioned single spiral release layer 6*a*, this double spiral release layer 6*a* could also be connected or fastened to the impenetrable part by gluing, welding or mechanically. In this embodiment, when pressing the inserter 11, not shown in FIG. 20, down for releasing of the combination 1, 2 from the packaging, the peripheral end 17 of each strip of the release layer 6*a* in the form of a tab are pressed down towards the impenetrable part 7 of the interior packaging and fastened with glue, said glue being placed at points corresponding to the tabs 17 within the interior of the packaging on the impenetrable part 7. When releasing the needle hub 1 and infusion part 2 from the packaging the release layer is then automatically peeled of the adhesive layer.

Figure 21:
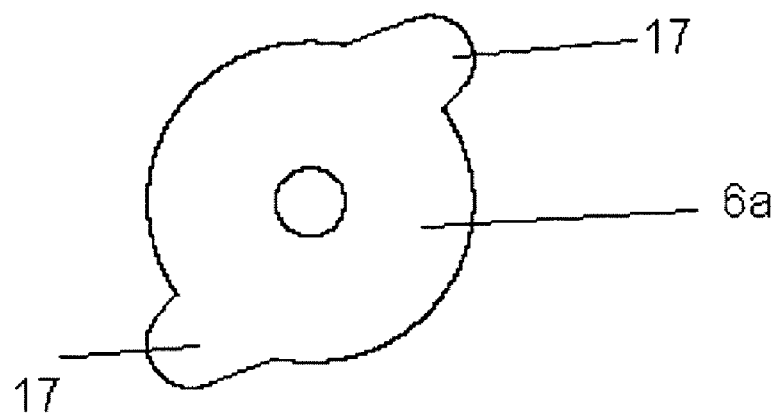
FIGS. 21a and 21b show two embodiments of the invention where the release paper covering the adhesive layer is formed as a surface covering the adhesive layer having two extending parts and a central opening.
Figure 21:
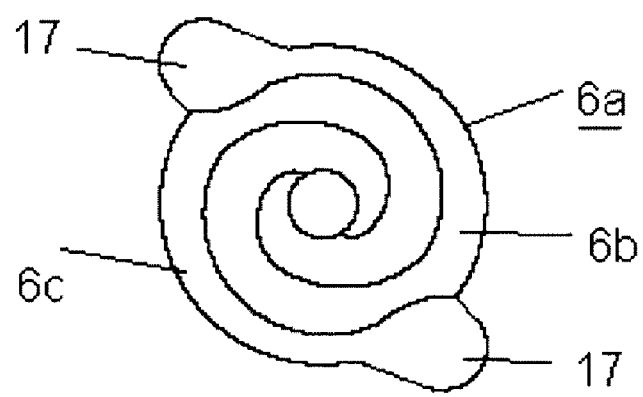

FIG. 21*a* shows one embodiment of the release layer 6*a* covering the adhesive layer, where the release layer 6*a* is in a single piece and has two extending peripheral ends 17 in the form of protruding tabs intended for fastening to the impenetrable part 7 or to a part integrated with the impenetrable part 7.

FIG. 21*b* shows another embodiment of the release layer 6*a* where the release layer is divided into two sections 6*b* and 6*c*, each section forming a strip such as a spiral band, thereby forming a double spiral release layer 6*a*. In this embodiment each extending peripheral end 17 of each strip of the release layer 6*a* are also in the form of protruding tabs 17 intended for fastening to the impenetrable part 7 or to a part integrated with the impenetrable part 7. This embodiment is a more suitable form of the release layer than the form shown in FIG. 21*a* as the strips defines a more precise length for the releasing of the release layer. Furthermore, by a single pull the release layer can be removed from the adhesive layer in two narrow strips and only little force is needed to remove it.

The invention claimed is:

1. Packaging for an infusion set comprising an infusion part and a needle hub, a proximal side of the infusion part is provided with an adhesive and the needle hub being combined with an insertion needle, the packaging comprising:

an impenetrable part including an inner part, the inner part comprising a retaining member for releasably retaining at least a portion of the infusion set in the impenetrable part, the impenetrable part comprising a support part surrounding a recess formed therein, the recess sized and shaped to contain the insertion needle, the support part configured to support at least a portion of the proximal side of the infusion part having the adhesive; and a removable part releasably connected to the impenetrable part; wherein the removable part is configured for removal from the impenetrable part prior to applying the infusion part to a patient's skin.

2. Packaging according to claim 1, wherein the retaining member is an integrated part of the impenetrable part.

3. Packaging according to claim 1, wherein the retaining member is a separate part.

4. Packaging according to claim 3, wherein the separate part is maintained in the impenetrable part when the infusion set is released from the packaging.

5. The packaging according to claim 1, further comprising an infusion set, the infusion set comprising an infusion part having a proximal side provided with an adhesive and a needle hub having an insertion needle, the infusion set positioned such that at least a portion of the proximal side is supported by the support part and the needle is contained within the recess.

6. Packaging according to claim 5, wherein the adhesive is covered with a release layer.

7. Packaging according to claim 6, wherein the release layer covering the adhesive is partly fastened to the impenetrable part or fastened to a part being connected to the impenetrable part.

8. Packaging according to claim 7, wherein the release layer comprises a band wherein one end of the band is fastened to the impenetrable part or fastened to a part being connected to the impenetrable part.

9. Packaging according to claim 7, wherein the release layer comprises at least two bands where one end of each band is fastened to the impenetrable part or fastened to a part being connected to the impenetrable part.

10. Packaging according to claim 5, wherein the needle hub is provided with means for retaining a device.

11. Packaging according to claim 5, wherein the needle hub comprises a retainer for retaining an inserter.

12. Packaging according to claim 5, wherein the needle hub comprises a retainer for retaining an inserter when the inserter is pushed towards the needle hub from a distal side of the inserter.

13. Packaging according to claim 1, wherein the impenetrable part comprises a hard material.

14. Packaging according to claim 13, wherein the impenetrable part comprises one of polypropylene (PP), polyethylene (PE HD) and polyvinyl chloride (PVC).

15. Packaging according to claim 1, wherein the retaining member is configured to releasably retain the infusion set and wherein the retaining member is formed as an integrated part of the impenetrable part of the packaging.

16. Packaging according to claim 15, wherein the retaining member of the impenetrable part is configured to releasably connect to a connector of the infusion part.

17. Packaging according to claim 15, wherein the retaining member comprises walls upstanding from the impenetrable part in an angle between −45° and 45° where 0° is orthogonal to a proximal surface of the impenetrable part.

18. Packaging according to claim 15, wherein the retaining member comprises a material wherein the material can be penetrated by the insertion needle and wherein the material is unreleasably connected to the impenetrable part of the packaging.

19. Packaging according to claim 1, wherein the retaining member is configured to releasably connect to a connector comprising a cylinder or a truncated cone integrated with the infusion part.

20. Packaging according to claim 19, wherein the connector comprises a cylinder or a truncated cone formed by a groove in the infusion part such that a proximal end of the connector is configured to be aligned to a proximal surface of the infusion part.

21. Packaging according to claim 1, wherein the support part is fastened to the impenetrable part or formed as an integrated part of the impenetrable part, the support part is configured to be parallel to a proximal surface of the infusion set.

22. Packaging according to claim 1, wherein the retaining member comprises an opening configured to receive the needle and a support part parallel to a proximal surface of the infusion set.

23. Packaging according to claim 22, wherein the opening is sized and shaped to receive a connector comprising a cylinder or a truncated cone protruding from the proximal surface of the infusion part.

* * * * *

UNITED STATES PATENT AND TRADEMARK OFFICE
CERTIFICATE OF CORRECTION

| | |
|---|---|
| PATENT NO. | : 7,621,395 B2 |
| APPLICATION NO. | : 11/450807 |
| DATED | : November 24, 2009 |
| INVENTOR(S) | : Lasse W. Mogensen et al. |

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 115 days.

Delete the phrase "by 115 days" and insert -- by 284 days --

Signed and Sealed this

Third Day of August, 2010

David J. Kappos
*Director of the United States Patent and Trademark Office*